US00PP13950P29

(12) United States Plant Patent
Stemkens

(10) Patent No.: US PP13,950 P2
(45) Date of Patent: Jul. 8, 2003

(54) DIASCIA PLANT NAMED 'DIASTIS'

(75) Inventor: Henricus G. W. Stemkens, Hoorn (NL)

(73) Assignee: Syngenta Seed B.V., Enkhuisen (NL)

( * ) Notice: Subject to any disclaimer, the term of this patent is extended or adjusted under 35 U.S.C. 154(b) by 0 days.

(21) Appl. No.: 10/041,239

(22) Filed: Jan. 7, 2002

(51) Int. Cl.[7] ..... A01H 5/00

(52) U.S. Cl. ..... Plt./263

(58) Field of Search ..... Plt./263, 272

*Primary Examiner*—Bruce R. Campell
*Assistant Examiner*—Annette H. Para
(74) *Attorney, Agent, or Firm*—Bruce Vrana; Edouard G. Lebel

(57) ABSTRACT

A new Diascia plant particularly distinguished by its large coral flower, early flowering, and a semi-erect habit that becomes spreading as plant develops.

1 Drawing Sheet

LATIN NAME OF THE GENUS AND SPECIES OF THE PLANT CLAIMED

*Diascia barbarae.*

VARIETY DENOMINATION

'DIASTIS'.

BACKGROUND OF THE NEW PLANT

The present invention comprises a new distinct cultivar of Diascia, botanically known as *Diascia barbarae*. The new cultivar is propagated from cuttings resulting from the cross of 'A 75-1' and 'A 64-1'. 'A 75-1' is a pink flowering Diascia having a spreading habit and very large flowers. 'A 75-1' is not commercially available and is not known by any synonyms. 'A 64-1' is a coral flowering Diascia having a semi-erect habit and intermediate flowersize. 'A 64-1' is not commercially available and is not known by any synonyms. Neither 'A 75-1' or 'A 64-1' has been patented. As a result of this cross the present cultivar was created in 1998 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Diascia plant is an annual in most climatical zones in the US.Only in zones 7, 8, 9 and 10 it is a perennial plant.

DESCRIPTION OF THE DRAWING

This new Diascia plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Diascia. The data which defines these characteristics were collected from asexual reproductions carried out in Enkhuizen, Netherlands. The plant history was taken on 10 weeks old plants, blossomed under natural light in a greenhouse. Color readings were taken in the greenhouse under ambient light. Color references are primarily to The R.H.S. Color Chart of The Royal Horticultural Society of London.

Differences between the new variety 'Diastis', its parents and a similar cultivar

| Character | 'Diastis' | 'A 75-1' | 'A 64-1' | 'Coral Belle' |
|---|---|---|---|---|
| Flower color | Deep coral | Pink | Coral | Coral |
| Flower size | 22–26 mm | 24–28 mm | 16–18 mm | 20–24 mm |
| Leaf color | Deep green | Deep green | Light green | Green |

The Plant

Classification — botanical: *Diascia barbarae.*
Parentage:
*Female parent.*—A seedling named 'A 75-1' is one of our seedlings from our A-generation of plants bred in 1996.
*Pollen parent.*—A seedling named 'A 64-1' is one of our seedlings from our A-generation of plants bred in 1996.
Growth habit: Semi-erect, later spreading.
Plant height: 24–30 cm.
Spreading area of plant: 40–60 cm.
Growth rate: Vigorous.
Strength: Very good.
Branching character: Freely branching and lateral branching at every node.
Quantity of branches: 150–170 branches per plant.
Blooming period: From April until November.

The Stem

Diameter: 0.5–1.0 mm.
Shape: Round.
Color: 141B.
Anthocyan pigmentation: Absent.
Length of internode:
*Vegetative growth.*—15–35 mm.
*Generative growth.*—25–55 mm.
Pubescence: Not pubescent.

The Foliage

Phyllotaxis: Opposite.
Shape of blade: Cordate to ovate.
Texture:
*Upper side.*—Smooth.
*Lower side.*—Smooth.
Attachment to leaf: Petiolate.
Venation: Pinnate.
Leaf margin: Serrate.
Leaf base: Truncate to subcordate.
Leaf apex: Acute.
Length: 18–26 mm.
Width: 12–22 mm.
Depth of incision: 10–20 mm. Color:
*Upper side.*—Medium green 141A.
*Lower side.*—Light green 147C.
Pubescence: No pubescence.
Length of petiole: 2–3 mm.
Color of petiole: Light green 141A.
Petiole surface structure: Smooth.

The Bud

Peduncle length: 20–40 mm, depending on season.
Peduncle shape: Long and threadlike.
Size:
*Diameter.*—3 mm.
*Length.*—3 mm.
Shape: Oval.
Color: Medium green 141B.
Sepals:
*Color.*—Medium green 141B.
*Form..*—Star-shaped.
*Number.*—5, parted.
*Size.*—1–2 mm.
*Shape.*—Elliptic, apex acute.
*Margin.*—Entire.
*Texture.*—Smooth.

The Flower

Flower width: 20–24 mm.
Flower length: 22–26 mm.
Flower depth: 10–14 mm.
Flower aspect: Tipped upward and outward.
Borne: Solitary.
Form: Zygomorphic, five lobed, double nectar spur.
Cluster: Raceme.
Color:
*Upper surface.*—Orange red 35B.
*Lower surface.*—Orange red 35C.
Overlapping of petals: Separate.
No. of petals: Five.
Shape of the petals: Two upper banner panels, two lateral petals and one larger basal lip petal. Base of two banner petals form a small yellow indentation (color yellow 9B) just above the reproductive organs. Center of two lateral petals form curved nectar spurs. Rounded lip petal is much larger and forms a nearly horizontal 'platform'.
Petal margin: Entire.
Petal surface texture: Smooth.
Size of the banner petals:
*Length.*—4–6 mm.
*Width.*—8–11 mm.
Size of the lateral petals:
*Length.*—4–6 mm.
*Width.*—7–9 mm.
Size of the basal lip petal:
*Length.*—15–17 mm.
*Width.*—15–17 mm.
Spur:
*Length.*—8 mm.
*Color.*—Greyed purple 184A.
No. of flowers per raceme: 20–25.
Fragrance: No fragrance.
Lastingness of the bloom: New florets continue to open in one raceme over a period of 20 days.
Lastingness of one flower: About 5 days depending on temperature.

Reproductive organs

Androecium:
*Stamen number.*—3.
*Anther shape.*—Two-lobed.
*Anther size.*—Less than 1 mm.
*Anther color.*—Yellow 7A.
*Amount of pollen.*—Very much pollen.
*Pollen color.*—Yellow 7A.
Gynoecium:
*Pistil number.*—1.
*Stigma shape.*—Rounded.
*Pistil length.*—2–3 mm.
*Style color.*—Green 144A.
*Stima color.*—Green white 157A.
*Ovary color.*—Green 144A.

Seeds

Seedset: No seedset has been observed.

Roots

Type of roots: Fibrous.
Root description: Fine and freely branching.

Physiological and ecological characteristics

Good tolerance to heat and cold.

What is claimed is:

1. A new and distinct variety of Diascia plant, substantially as herein illustrated and described, characterized particularly as to novelty by coral flowers, which appear earlier on the plant, which produces no seeds, and has a growing habit that is first semi-erect but later spreading and hanging.

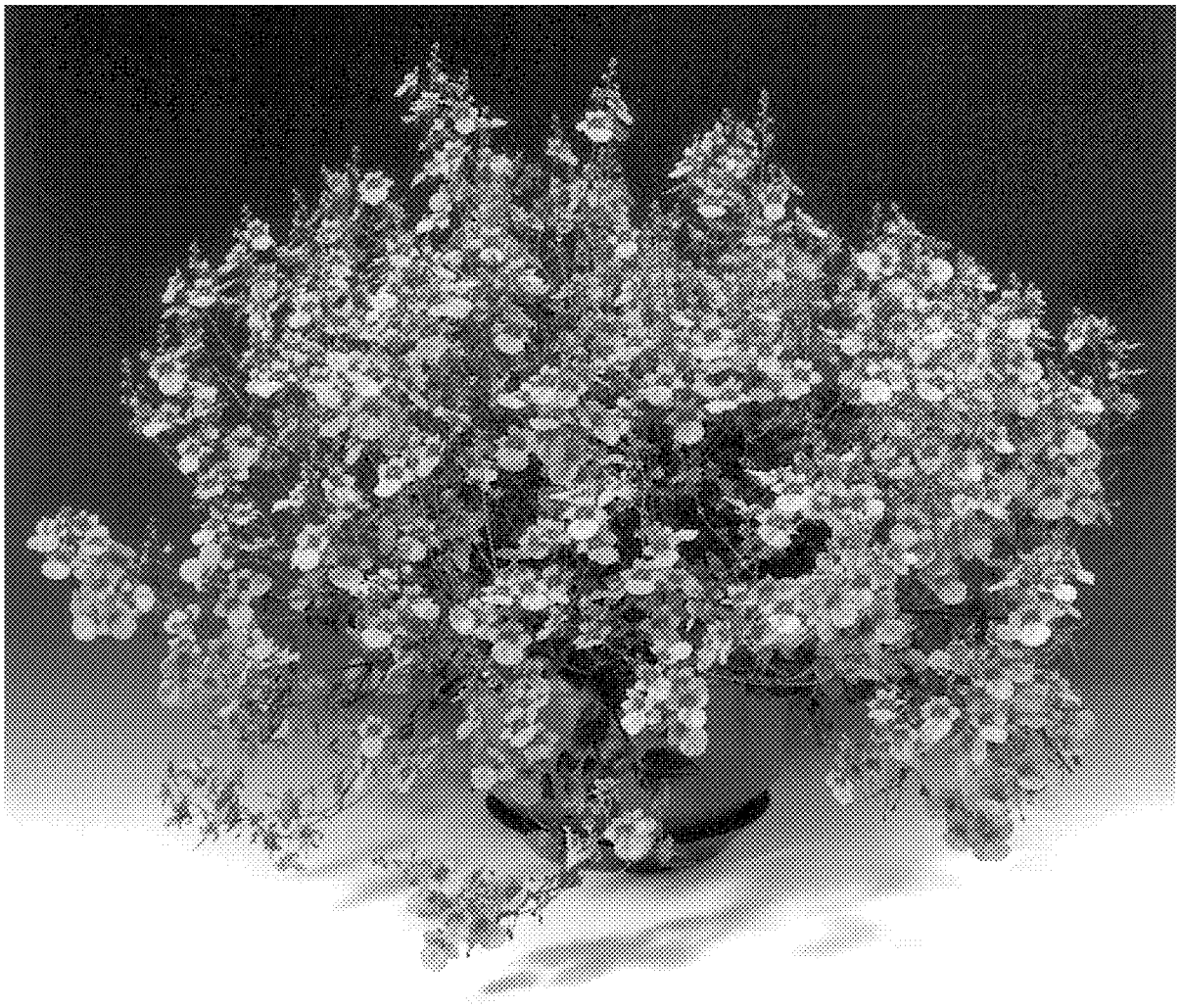

* * * * *